United States Patent [19]

Harde et al.

[11] Patent Number: 5,502,028
[45] Date of Patent: Mar. 26, 1996

[54] HERBICIDAL PYRIMIDINYL OR TRIAZINYL HALOACETIC ACID DERIVATIVES

[75] Inventors: Christoph Harde; Gerhard Johann; Gabriele Krüger; Richard Rees; Gerhard Tarara, all of Berlin, Germany; Peter S. Gates, Cambridge, England

[73] Assignee: Schering Agrochemicals Limited, England

[21] Appl. No.: 357,526

[22] Filed: Dec. 16, 1994

Related U.S. Application Data

[63] Continuation of Ser. No. 119,048, filed as PCT/GB92/00376, Mar. 13, 1991.

[30] Foreign Application Priority Data

Mar. 13, 1991 [GB] United Kingdom .................. 9105297

[51] Int. Cl.⁶ .......................... A01N 43/54; A01N 43/66; C07D 239/52; C07D 251/20
[52] U.S. Cl. .......................... 504/227; 504/243; 544/219; 544/319
[58] Field of Search ................... 504/239, 240, 504/241, 242, 243, 227, 228, 230, 231, 232, 234; 544/319, 219

[56] References Cited

U.S. PATENT DOCUMENTS

| | | | |
|---|---|---|---|
| 3,062,818 | 11/1962 | Schaefer et al. .................. | 260/248 |
| 5,098,465 | 3/1992 | Krüger et al. .................. | 71/93 |
| 5,137,564 | 8/1992 | Jones .................. | 71/92 |

FOREIGN PATENT DOCUMENTS

| | | |
|---|---|---|
| 0353640 | 2/1990 | European Pat. Off. . |
| 0410590 | 1/1991 | European Pat. Off. . |

*Primary Examiner*—S. Mark Clardy
*Attorney, Agent, or Firm*—Ostrolenk, Faber, Gerb & Soffen

[57] ABSTRACT

Herbicidal haloacetic acid derivatives of the formula:

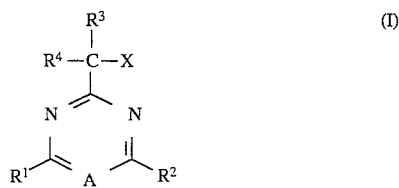

and salts thereof, where:

A is —N= or —CH=;

X is halo;

$R^1$ and $R^2$, which may be the same or different, each represent alkyl, alkoxy, haloalkyl, haloalkoxy, halo, alkylamino or dialkylamino;

$R^3$ is —CN, —COOR⁵, —CONR⁶R⁷, —CSNH₂, —CHO, —CH=Z, —CH(OAlkyl)₂, —CH₂OH, —CH₂OR⁹, or a substituted or unsubstituted 5- or 6-membered heterocyclic group linked via a ring carbon atom which is between two ring heteroatoms;

$R^4$ is H, or a substituted or unsubstituted alkyl, alkenyl, alkynyl, cycloalkyl, aryl or aralkyl group;

with $R^5$, $R^6$, $R^7$, $R^9$, and Z as defined in the specification.

25 Claims, No Drawings

HERBICIDAL PYRIMIDINYL OR TRIAZINYL HALOACETIC ACID DERIVATIVES

This is a Continuation of application Ser. No. 08/119,048 which was filed on Sept. 10, 1993 under 35 USL 371 from PCT/GB92/00376, which was filed on Mar. 3, 1992.

FIELD OF THE INVENTION

This invention concerns new haloacetic acid derivatives having herbicidal activity, processes for their preparation and herbicidal compositions containing them.

PRIOR ART

Certain pyrimidinyl and triazinyl acetic acid derivatives having herbicidal activity have previously been described, for example in our earlier European Patent specification no 410590.

DESCRIPTION

In one aspect, this invention provides the compounds of the formula:

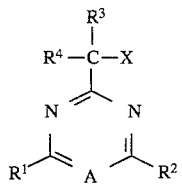

(I)

and salts thereof, where:

A is —N= or —CH=;

X is halo;

$R^1$ and $R^2$, which may be the same or different, each represent alkyl, alkoxy, haloalkyl, haloalkoxy, halo, alkylamino or dialkylamino;

$R^3$ is —CN, —COOR$^5$, —CONR$^6$R$^7$, —CSNH$_2$, —CHO, —CH=Z, —CH(OAlkyl)$_2$, —CH$_2$OH, —CH$_2$OR$^9$, or a substituted or unsubstituted 5- or 6-membered heterocyclic group linked via a ring carbon atom which is between two ring heteroatoms;

$R^4$ is H, or a substituted or unsubstituted alkyl, alkenyl, alkynyl, cycloalkyl, aryl or aralkyl group;

$R^5$ is H, —N=CR$^{6a}$R$^{6b}$, or a substituted or unsubstituted alkyl, alkenyl, alkynyl, cycloalkyl or aralkyl group;

$R^6$ is H, or a substituted or unsubstituted alkyl, alkenyl, alkynyl, cycloalkyl, aryl, aralkyl or heteroaryl group;

$R^7$ is a group as defined for $R^6$ or is —SO$_2$R$^8$ —OH, —CN, —OR$^{10}$, —NH$_2$ or —NHR$^{10}$; or $R^6$ and $R^7$ together form a ring;

$R^8$ is —NR$^{6a}$R$^{6b}$ or a substituted or unsubstituted alkyl, alkenyl, alkynyl, cycloalkyl, aralkyl, aryl or heteroaryl group;

$R^9$ is a substituted or unsubstituted alkyl, alkenyl, alkynyl, cycloalkyl, aralkyl or acyl group;

$R^{10}$ is a group as defined for $R^9$, or is a substituted or unsubstituted aryl or heteroaryl group;

Z is =N—NR$^6$R$^{12}$ or =NOR$^6$;

$R^{12}$ is a group as defined for $R^6$ or is a substituted or unsubstituted acyl group; and $R^{6a}$ and $R^{6b}$, which may be the same or different, are each a group as defined for $R^6$;

with the proviso that, when $R^4$ is ortho-substituted phenyl or naphthyl, any ortho-substituent thereon is halogen, —NO$_2$, —OH, —OR$^{10}$, —SH, —SR$^8$, —SOR$^8$, —SO$_2$R$^8$, —NH$_2$, —NR$^6$R$^{10}$, aryl or heteroaryl.

Any alkyl group present in the molecule is preferably of 1 to 8 carbon atoms, especially of 1 to 6 carbon atoms, and particularly of 1 to 4 carbon atoms. Specific preferred unsubstituted alkyl or alkyl-containing groups include methyl, ethyl, n-propyl, isopropyl, n-butyl, t-butyl, methoxy, ethoxy and n-propoxy.

When any alkyl group in the molecule is substituted, this may for example be by one or more halogen atoms (eg fluorine, chlorine or bromine), alkoxy groups of 1 to 4 carbon atoms (eg methoxy or ethoxy), hydroxy, nitro, mercapto, amino, substituted amino, cyano, acyl, aryl or heteroaryl groups, or groups of the formula —SR$^8$ or —SOR$^8$. Specific preferred substituted alkyl-containing groups include chloromethyl, bromomethyl, dichloromethyl, trifluoromethyl, difluoromethoxy, methoxyethyl and ethoxyethyl.

Any alkenyl or alkynyl group present in the molecule is preferably of 2 to 6 carbon atoms, for example allyl, vinyl or propargyl. Any such alkenyl or alkynyl group is preferably unsubstituted, though it may if desired be substituted for example by halogen.

Any cycloalkyl group present in the molecule is preferably of 3 to 7 carbon atoms, especially cyclopentyl or cyclohexyl. It is preferably unsubstituted.

Any halogen atom present in the molecule is preferably fluorine, chlorine or bromine.

The term 'aryl' is used herein to mean aromatic carbocycles, which may be mononuclear, eg phenyl, or polynuclear, eg naphthyl. Any aryl group present in the molecule is preferably a substituted or unsubstituted phenyl group. Accordingly, any aralkyl group present in the molecule is preferably a substituted or unsubstituted benzyl group.

Any aryl group present in the molecule, when substituted, is preferably substituted by one or more halogen atoms (eg fluorine, chlorine or bromine), alkyl or alkoxy groups of 1 to 4 carbon atoms (eg methyl, ethyl, methoxy or ethoxy), hydroxy, nitro, mercapto, amino, substituted amino (eg alkylamino, dialkylamino or acylamino groups, especially where the alkyl moieties have from 1 to 4 carbon atoms), cyano, acyl, aryl or heteroaryl groups, or groups of the formula —SR$^8$ or —SOR$^8$.

The term 'heteroaryl' is used herein to mean aromatic heterocyclic groups, which may be mononuclear or polynuclear. Mononuclear heterocyclic groups are preferably of 5 or 6 ring atoms and contain at least one atom of nitrogen, oxygen or sulfur, eg furyl, thienyl, pyrrolyl, oxazolyl, thiazolyl, imidazolyl, pyrazolyl, pyridinyl, pyrazinyl or thiadiazolyl. Polynuclear heterocyclic groups are preferably benzoheterocyclic groups, eg indolyl, benzofuranyl, benzimidazolyl or quinolinyl. Such mononuclear or polynuclear heterocyclic groups may, if desired, be substituted eg by one or more halogen atoms, eg chlorine, fluorine or bromine atoms, nitro groups, substituted or unsubstituted amino groups (eg alkylamino, dialkylamino or acylamino groups, especially where the alkyl moieties-have from 1 to 4 carbon atoms), cyano groups, or alkyl or alkoxy groups of 1 to 4 carbon atoms, eg methyl, ethyl, methoxy or ethoxy.

The term 'acyl' is used herein to mean the residue of carboxylic, sulfonic or phosphorus-containing acids, for example alkanoyl, alkenoyl, alkynoyl, cycloalkanoyl, aralkanoyl, aroyl, carbamoyl, thiocarbamoyl, alkoxycarbonyl, sulfonyl, sulfamoyl and phosphonyl groups, in which any alkyl, alkenyl, alkynyl or aryl group may be substituted or unsubstituted.

The salts of the compounds of formula I are preferably those formed with alkali-metals (eg lithium, sodium or potassium), ammonium salts, or those formed with organic amines such as cyclohexylamine or piperidine.

A preferably represents —CH=.

X preferably represents chlorine, fluorine or bromine, especially fluorine.

$R^1$ is preferably chloro, methyl, methoxy, difluoromethoxy or ethoxy, especially methoxy.

$R^2$ is preferably methyl, methoxy or difluoromethoxy, especially methoxy.

$R^3$ is preferably a group —COOR$^5$ where $R^5$ is optionally-substituted alkyl of 1 to 4 carbon atoms, especially methyl, ethyl or tetrahydrofurylmethyl. Examples of other groups which $R^3$ may advantageously represent include —CONR$^6$R$^7$ (where $R^6$ is hydrogen and $R^7$ is SO$_2$CH$_3$, SO$_2$N(CH$_3$)$_2$, NH$_2$, phenyl or 3-pyridyl, or where $R^6$ and $R^7$ together with the nitrogen atom to which they are attached form a ring, eg a morpholino group), —CH=Z (where Z is NNHCOCH$_3$ or NOCH$_2$CO$_2$C$_2$H$_5$), —CH(OCH$_3$)$_2$, —CH$_2$OR$^9$ (where $R^9$ is CH$_2$CO$_2$C$_2$H$_5$ or SO$_2$CH$_3$), or a dioxolan, thiazolyl or oxadiazolinone ring.

$R^4$ is preferably an unsubstituted alkyl group, especially isopropyl, sec-butyl or an aryl group, especially phenyl.

Specific preferred compounds according to the invention are those of the Examples provided hereinafter.

The compounds of formula I where $R^3$ represents a group —COOR$^5$ (in which $R^5$ is other than hydrogen), and $R^4$ represents hydrogen can be prepared by a process in which a compound of the formula:

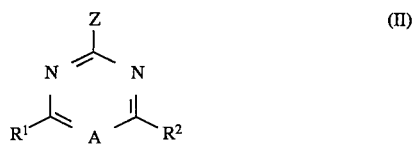

where

A, $R^1$ and $R^2$ are as defined hereinbefore, and Z is an anionic leaving group, for example halo or a group of formula —SO$_2$Z' where Z' is alkyl of 1 to 4 carbon atoms or aryl, is reacted in the presence of a base with a compound of the formula XCH$_2$COOR$^5$(where $R^5$ is as defined hereinbefore but is other than hydrogen, and X is halogen) to give the desired compound.

The base employed is preferably lithium diisopropylamide, and the reaction is desirably effected in a suitable solvent medium, eg tetrahydrofuran, and with cooling, eg to about −78° C.

The compounds of formula I where $R^3$ represents a group —CN, —COOR$^5$ or —CONR$^6$R$^7$ may also be prepared by a process in which a compound of the formula:

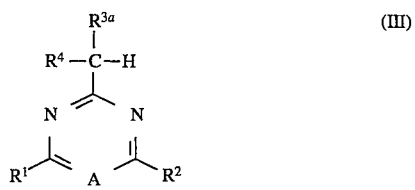

where

A, $R^1$, $R^2$ and $R^4$ are as defined hereinbefore, and $R^{3a}$ is —CN, —COOR$^5$ or —CONR$^6$R$^7$ (where $R^5$, $R^6$ and $R^7$ are as defined hereinbefore) is halogenated to give the desired compound.

The halogenation may be effected by conventional techniques depending on the nature of the halogen involved. For example, bromination may be effected by means of N-bromosuccinimide. Fluorination may be effected by first subjecting the compound of formula III to the action of a strong base, eg sodium hydride or lithium diisopropylamide, and reacting the formed anion with a fluorinating agent, eg N-fluoro-N-propyl-p-toluenesulfonamide or N-fluoro-N'-chloromethyl-triethylenediamine salts.

Compounds of formula III and processes for their preparation are described in European Patent specification no 410590. Any compounds of formula III not described therein may be made by processes analogous to those described.

The compounds of formula I where $R^3$ represents a group —CN, —COOR$^5$, —CHO or —CH$_2$OH, and $R^1$ and $R^2$ each represent alkyl, alkoxy, alkylamino or dialkylamino, may also be prepared by a process in which a compound of the formula:

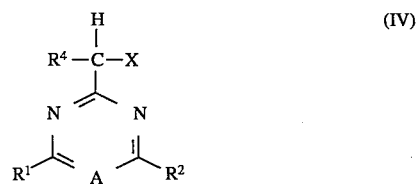

where $R^1$, $R^2$, $R^4$, X and A are as defined hereinbefore is subjected to the action of a suitable electrophile in the presence of a strong base, to give the desired compound.

The strong base employed may, for example, be butyl-lithium or lithium diisopropylamide, and the reaction is desirably effected at reduced temperature, eg at −78° C., and in a suitable solvent medium, eg tetrahydrofuran.

Suitable electrophiles include cyanates (eg phenyl cyanate), chloroformates (eg alkyl chloroformates), aldehydes (eg formaldehyde) and formamides (eg formdimethylamide).

The compounds of formula IV where $R^1$ and $R^2$ are alkyl may be made by standard methods. The compounds of formula IV where $R^1$ and $R^2$ are alkoxy, alkylamino or dialkylamino may be prepared by reaction of a carboxylic acid derivative of the formula $R^4$—CH(X)—W, where $R^4$ and X are as defined hereinbefore and W is an acid, ester, acid chloride, amide or nitrile group, with a compound of the formula $R^1$—C(=NH)—A—C(=NH)—R$^2$ where $R^1$, $R^2$ and A are as defined hereinbefore.

The compounds of formula I where $R^4$ is other than hydrogen can be prepared from the corresponding compounds in which $R^4$ is hydrogen by alkylation or arylation techniques known per se, or by analogous processes well known to those skilled in the art.

The compounds of formula I where $R^3$ is other than —CN, —COOR$^5$ or —CONR$^6$R$^7$ as defined hereinbefore, may be prepared from such compounds by conventional techniques well known to those skilled in the art.

In particular, the compounds of formula I where $R^3$ is carboxy can of course be prepared from the corresponding esters by hydrolysis, and many further conversions of the acid or ester function can be effected in known ways.

For example, the compounds of formula I where $R^3$ is a group —COOR$^5$ may be reduced, eg by means of diisobutylaluminium hydride, to the corresponding compounds where $R^3$ is a group —CHO (using one molar proportion of the hydride) or —CH$_2$OH (using two molar proportions of the hydride). The reductions are conveniently effected in a suitable solvent medium, eg tetrahydrofuran, and with cooling, eg to 5° C.

The compounds of formula I where $R^3$ is —$CH_2OH$ can be acylated or etherified to give the corresponding compounds where $R^3$ is a group —$CH_2OR^9$.

The compounds of formula I where $R^3$ is —CHO can be converted by known techniques to the corresponding hydrazones (eg by reaction with a compound of formula $H_2N$—$NR^6R^{12}$ in a suitable solvent medium, eg an alcohol), oximes (eg by reaction with a compound of formula $H_2NOR^6$ in a suitable solvent medium, eg an alcohol), ketals, 1,3-dioxolanes, 1,3-dithiolanes, 1,3-dioxanes, 1,3-dithianes or imidazolidines (eg by heating in the presence of an acid catalyst with a compound of formula RQH or HQ—$(CH_2)_{2-3}$—QH where Q is O, S or NH).

In addition, the compounds of formula I where $R^3$ is carboxy may be converted to the corresponding compounds in which $R^3$ is a group —$CONHSO_2R^8$ by a two-stage process in which the acid is first reacted with thionyl chloride to give the corresponding acyl chloride, and this is then reacted with a compound of the formula $NaNHSO_2R^8$ to give the desired compound.

The salts of the compounds of formula I may be prepared by reaction of the corresponding unsalified compound of formula I with an appropriate salt-forming base by methods known per se.

The compounds of formula I where $R^3$ is —CN can be converted by known techniques into the corresponding thioamides where $R^3$ is —$CSNH_2$ (eg by reaction with hydrogen sulfide in a suitable base such as pyridine).

The compounds of formula I where $R^3$ is a heterocycle may be prepared by ring closure procedures well known per se carried out on the corresponding compounds of formula I where $R^3$ is —CN, —$CSNH_2$ or —$CONR^6R^7$. For example, the compounds of formula I where $R^3$ is —CN may be converted by the action of ammonia into the corresponding compounds where $R^3$ represents —$C(=NH)NH_2$ which may be further reacted with α-haloketones, α-haloacid chlorides or β-diketones to give, respectively, the corresponding imidazoles, imidazolones and pyrimidines. Similarly, ring closure reactions may be performed on the compounds of formula I where $R^3$ represents —$CSNH_2$ for example by reaction thereof with dibromoethane, or on the compounds of formula I where $R^3$ is —$CONR^6R^7$ for example by reaction thereof with an acid chloride or anhydride.

The compounds of formula I and the salts thereof are herbicidally-active against a wide range of broadleaf and grass weeds, but are comparatively safe to certain crop species. They may thus be of use as herbicides, and especially as selective herbicides, particularly in cereals, eg maize, wheat or rice, in beet crops, eg sugar beet, in soybeans or in cotton.

In another aspect, therefore, this invention provides a herbicidal composition which comprises one or more compounds of formula I or salts thereof in association with a suitable carrier and/or surface active agent.

The compositions of the invention usually contain from 0.01 to 99% by weight of the present compounds, and are normally produced initially as concentrates containing from, 0.5 to 99%, preferably from 0.5 to 85%, and especially from 10 to 50% by weight thereof. Such concentrates are diluted if necessary before application to the locus to be treated such that the active ingredient comprises from 0.01 to 5% by weight of the formulation applied.

The carrier may be water, in which case an organic solvent may also be present, though this is not usually employed. A flowable suspension concentrate may be formed by grinding the compound with water, a wetting agent and a suspending agent, e.g. xanthan gum.

The carrier may alternatively be a water immiscible organic solvent, e.g. a hydrocarbon which boils within the range 130°–270° C., e.g. xylene, in which the compound is dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent e.g. 2-methoxyethanol, methanol, propylene glycol, diethylene glycol, diethylene glycol monoethyl ether, methylformamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulfonates and solid fertilizers. The carrier can be natural or synthetic or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, e.g. a polyhalogenated alkane such as dichlorofluoromethane, and suitably also with a solvent.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters, fatty alcohol sulfates such as sodium dodecyl sulfate, ethoxylated fatty alcohol sulfates, ethoxylated alkylphenol sulfates, lignin sulfates, petroleum sulfonates, alkylaryl sulfonates such as alkyl-benzene sulfonates or lower alkylnaphthalene sulfonates, salts of sulfonated naphthaleneformaldehyde condensates, salts of sulfonated phenolformaldehyde condensates, or more complex sulfonates such as the amide sulfonates, e.g. the sulfonated condensation product of oleic acid and N-methyl taurine or the dialkyl sulfosuccinates e.g. the sodium sulfonate of dioctyl succinate.

The surface active agents may also comprise non-ionic agents, for example condensation products or fatty acid esters, fatty alcohols, fatty acid amides or alkali-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethyl-ammonium bromide, or ethoxylated tertiary fatty amines.

Preferred surface active agents include ethoxylated fatty alcohol sulfates, lignin sulfonates, alkyl-aryl sulfonates, salts of sulfonated naphthaleneformaldehyde condensates, salts of sulfonated phenolformaldehyde condensates, sodium oleoyl N-methyltauride, dialkyl sulfosuccinates, alkyl phenol ethoxylates, and fatty alkyl ethoxylates.

The present active compounds may be admixed with another pesticide, eg a herbicide, fungicide or insecticide, or a plant growth regulator, particularly another herbicide.

Suitable further herbicides include trietazine, linuron, MCPA, dichlorprop, isoxaben, diflufenican, metolachlor, fluometuron, oxyfluorfen, fomesafen, bentazone, prometryne, norflurazon, chlomazone, EPTC, imazaquin, and especially isoproturon, methabenzthiazuron, trifluralin, ioxynil, bromoxynil, benazolin, mecoprop, fluroxypyr, alachlor, acifluorfen, lactofen, metribuzin, pendimethalin, ethofumesate, benfuresate, phenmedipham, benzophenap, butachlor, chlomethoxyfen, dimepiperate, mefenacet, molinate, naproanilide, oxadiazon, piperophos, prometryne, pyrazoxyfen, pyrazosulfuron-ethyl, bensulfuron, simetryne, pyrazolate, pretilachlor, thiobencarb and pyributicarb.

The present compounds may be applied to plants, the soil, land or aquatic areas, and particularly to a locus at which a crop is growing. The compounds are active both pre- and post-emergence, and may be employed at rates of from 1 g to 2kg/ha.

EXAMPLES

The invention is illustrated by the following Examples, in which Me=methyl, Et=ethyl, Pr=propyl, Bu=butyl, s-Bu=1-methylpropyl, Oct=octyl, cyhex=cyclohexyl, THF=tetrahydrofuryl and Ph=phenyl.

EXAMPLE 1

Ethyl 2-fluoro-2-(4,6-dimethoxypyrimidin-2-yl)acetate

Butyllithium (21ml of a 1.6M solution in hexane) was added to di-isopropylamine (4.94ml) in dry tetrahydrofuran (100ml) under nitrogen at a temperature of −78° C., and the mixture was stirred for 30 minutes. A solution of ethyl fluoroacetate (2.51g) in dry tetrahydrofuran (20ml) was then added at a temperature of −60° C., and the mixture was stirred for 1 hour. Hexamethylphosphoric triamide (5.12ml) was added, and the mixture was stirred for a further 10 minutes. Then 4,6-dimethoxy-2methylsulfonylpyrimidine (5.0g) was added portionwise, and the temperature of the reaction mixture rose within 2.5 hours to room temperature. The reaction mixture was washed with saturated ammonium chloride and sodium chloride solution, the aqueous phase was extracted with ethyl acetate, and the combined organic layers were dried over magnesium sulfate and evaporated. The product obtained was chromatographed on silica gel using hexane/ethyl acetate (0–20% ethyl acetate), to give the desired compound as a yellow oil (0.56g), refractive index at 20° C. =1.4829.

EXAMPLE 2

Ethyl 2-(4,6-dimethoxypyrimidin-2-yl)-2-fluoro-3-methylbutanoate

Butyllithium (12.8ml of a 1.6M solution in hexane) was added to di-isopropylamine (3.05ml) in dry tetrahydrofuran (120ml) under nitrogen at a temperature of −78° C. and the mixture was stirred for 30 minutes. The product of Example 1 (3.4g) in dry tetrahydrofuran (20ml) was then added at a temperature of −65° C., and the mixture was stirred for 1 hour, during which the temperature rose to −30° C. After cooling to −60° C., 3.18 g of hexamethylphosphoric triamide were added, and the mixture was stirred for 15 minutes. Then 2-iodopropane (3.4 g) was added, and the mixture was stirred at room temperature for 72 hours, after which it was diluted with 100ml diethyl ether, and washed with a saturated ammonium chloride and sodium chloride solution. The aqueous phase was extracted with diethyl ether, and the organic layer was dried over magnesium sulfate and evaporated. The yellow oil obtained was finally chromatographed on silica gel using hexane/ethyl acetate (0–5% ethyl acetate) to give 1.46 g of the desired product, refractive index at 20° C. =1.4756.

EXAMPLE 3

Methyl 2, (4,6-dimethoxypyrimidin-2-yl)-2-fluoro-2-phenylacetate

Method A

Methyl 2-(4,6-dimethoxypyrimidin-2-yl) -2-phenylacetate (1.2 g) was dissolved in tetrahydrofuran (25ml), the solution was cooled to 5° C., and n-butyllithium (2.5M in hexane; 1.7ml) was added dropwise. The solution was stirred for 20 minutes and was then diluted with toluene (14ml). N-fluoro-N-propyltoluenesulfonamide (1.5 g) was added, and the solution was stirred for 20 hours under nitrogen at room temperature, then poured into saturated ammonium chloride solution (300 ml). It was extracted with ether, and the organic layer was washed and dried, then evaporated to dryness. The residue was purified by column chromatography on silica eluting with 15% ether in petrol 60–80, giving the desired product, 0.95 g, as a yellow oil.

Method B (a) 4,6-Dimethoxy-2-(α-fluorobenzyl) pyrimidine

Dimethyl malonimidate dihydrochloride (11.0 g) was suspended in dichloromethane (100 ml) at −40° C. Ethyl diisopropylamine (38.9 ml) was added dropwise over 15 minutes at −40° C., followed by 2-fluoro-2-phenylacetyl chloride (11.0 g) in dichloromethane (15 ml) over 10 minutes at −40° C. The reaction mixture was allowed to warm to room temperature and stand overnight. It was then diluted further with dichloromethane, washed with ammonium chloride solution, then with water, and was dried over magnesium sulfate. The dichloromethane solution was evaporated to dryness to give 13.9 g of the desired product.

(b) Methyl 2-(4,6-dimethoxypyrimidin-2-yl)-2-fluoro-2-phenylacetate n-Butyllithium (2.5M in hexane, 1.7 ml) was added to diisopropylamine (0.59 ml) under nitrogen in dry tetrahydrofuran (15 ml) at −78° C. This solution was stirred for 30 minutes, then a solution of the product of stage (a) above (1.0 g) in tetrahydrofuran (10 ml) was added over 20 minutes. Methyl chloroformate (0.4 g) in dry tetrahydrofuran (10 ml) was added over 15 minutes at −78° C., and the reaction mixture was allowed to warm slowly to room temperature, after which it was added to aqueous ammonium chloride solution. The mixture was extracted with ether, the extracts being washed with water, dried over magnesium sulfate, and evaporated to dryness to give 1.08 g of the desired product, identical to that of Method A above.

EXAMPLE 4

Methyl 2-chloro-2-(4,6-dimethoxypyrimidin-2-yl)-2-phenylacetate

Methyl 2-(4,6-dimethoxypyrimidin-2-yl)-2-phenylacetate (2.0 g) and N-chlorosuccinimide (2.0 g) were stirred at reflux in carbon tetrachloride (25 ml) under a bright light for 18 hours. The reaction mixture was filtered and evaporated to dryness, and the residue was purified by column chromatography on silica eluting with ether:hexane (1:1), yielding the desired product (2.16 g) as a pale yellow oil.

EXAMPLE 5

2-Fluoro-3-methyl-2,
(4,6-dimethoxy-1,3,5-triazin-2yl)butan-1-ol

Ethyl 2-fluoro-3-methyl-2-(4,6-dimethoxy-1,3,5-triazin2-yl)butanoate (1.5 g) (see Example 11 below) was dissolved in tetrahydrofuran (40 ml), and the solution was cooled to 5° C. under nitrogen. Di-isobutyl aluminium hydride (11 ml of 1.0M in hexane) was added, and the mixture was stirred for 24 hours at room temperature, after which it was treated dropwise with water (5 ml). The solution was stirred for a further 30 minutes, and silica (10 g) was added. The suspension was filtered, and the solution was dried and evaporated. The residue was purified by chromatography, yielding the desired compound (0.22 g) as a white solid, mp 72°–75° C.

EXAMPLE 6

2-Fluoro-3-methyl-2-(4,6-dimethoxy-1,3,5-triazin-2-yl)butyl acetate

The product of Example 5 (0.60 g) was dissolved in dry ether (40 ml) with triethylamine (0.35 ml) at 5° C., and acetyl chloride (0.18 ml) in dry ether (10 ml) was added dropwise. The solution was left to stand at room temperature for 2 days, after which it was filtered, and the organic layer was washed with water and dried. The residue was purified by chromatography, giving 0.35 g of the desired product as a clear oil.

EXAMPLE 7

2-Fluoro-3-methyl-2(4,6-dimethoxypyrimidin-2-yl)butanoic acid

Methyl 2-fluoro-3-methyl-2-(4,6-dimethoxypyrimidin-2yl)butanoate (1.0 g) (see Example 9 below) was dissolved in methanol (7 ml), and was treated with 5N sodium hydroxide solution (1.5 ml) at 5°–10° C. The methanol was evaporated off, and the residue was treated with water, then made acid with 5N hydrochloric acid, saturated with sodium chloride, and extracted with ether. The ethereal solution was washed with saturated sodium chloride solution and dried over magnesium sulfate. The product obtained by evaporation of the ether was triturated with pentane, yielding the desired product (0.87 g).

EXAMPLES 8–48

The following compounds of formula I in which $R^1$ and $R^2$ are both methoxy may be prepared by methods analogous to those of the above Examples:

| No | A | $R^3$ | $R^4$ | X | |
|---|---|---|---|---|---|
| | | Analogous to method of Example 1 | | | |
| 8 | N | COOEt | H | F | yellow oil |
| | | Analogous to method of Example 2 | | | |
| 9 | CH | COOMe | i-Pr | F | rd 1.4762 |
| 10 | CH | COOEt | s-Bu | F | colourless oil |
| 11 | N | COOEt | i-Pr | F | mp 48–49° C. |
| 12 | N | COOEt | s-Bu | F | yellow oil |
| 13 | N | COOEt | CH(Et)$_2$ | F | bp 160° C./0.1 mm Hg |
| 14 | N | COOEt | CH$_2$COt-Bu | F | pale yellow gum |
| 15 | N | COOEt | n-Pr | F | pale yellow gum |
| 16 | N | COOEt | CH(Me)Ph | F | pale yellow gum |
| 17 | N | COOEt | CH(Me)COOEt | F | pale yellow gum |
| 18 | N | COOEt | CH(Me)CN | F | pale yellow gum |
| 19 | N | COOEt | CH(Me)COMe | F | pale orange oil |
| | | Analogous to method of Example 3 (Method B) | | | |
| 20 | CH | COOn-pentyl | Ph | F | yellow oil |
| | | Analogous to method of Example 4 | | | |
| 21 | CH | COOMe | H | Br | mp 74–76° C. |
| 22 | CH | COOMe | Ph | Br | pale yellow oil |
| | | Various appropriate methods | | | |
| 23 | CH | COOn-Oct | s-Bu | F | |
| 24 | CH | COON=C(Me)$_2$ | Ph | F | |
| 25 | CH | CONHSO$_2$Me | Ph | F | |
| 26 | CH | COON=C(Me)$_2$ | 2-MePh | F | |
| 27 | CH | 2-COOCH$_2$THF | 3-MePh | F | |
| 28 | CH | CHO | Ph | F | |
| 29 | CH | 1,3-dioxolan-2-yl | Ph | F | |
| 30 | CH | 4,5-dihydro-5-oxo-1,2,4-oxadiazol-3-yl | i-Pr | F | |
| 31 | CH | 4,5-dihydrothiazol-2-yl | 1-naphthyl | F | |
| 32 | CH | CH$_2$OH | Ph | F | |
| 33 | CH | CH$_2$OCH$_2$COOEt | i-Pr | F | |
| 34 | CH | CH$_2$OSO$_2$Me | s-Bu | F | |
| 35 | N | COOn-Bu | i-Pr | F | |
| 36 | N | CN | Ph | F | |
| 37 | N | CH=NNHCOMe | Ph | F | |
| 38 | N | CONHNH$_2$ | Ph | F | |
| 39 | N | COOn-Bu | Ph | Cl | |
| 40 | CH | CH=NOCH$_2$COOEt | n-Pr | F | |

-continued

| No | A | R³ | R⁴ | X |
|---|---|---|---|---|
| 41 | N | CONHPh | cyhex | F |
| 42 | CH | COOn-Bu | i-Pr | F |

The following compounds of formula I where $R^1$ and $R^2$ are both methyl may be prepared by methods analogous to those described above:

| 43 | CH | CONHSO₂Me | i-Pr | F |
|---|---|---|---|---|
| 44 | CH | CONHSO₂N(Me)₂ | Ph | F |

The following compound of formula I where $R^1$ is chloro and $R^2$ is methoxy may be prepared by methods analogous to those described above:

| 45 | CH | COOEt | CH≡CCH₂ | F |
|---|---|---|---|---|

The following compounds of formula I where $R^1$ and $R^2$ are both difluoromethoxy may be prepared by methods analogous to those described above:

| 46 | CH | COOEt | 2-ClPh | F |
|---|---|---|---|---|
| 47 | CH | COOCH₂Ph | 3-ClPh | F |

-continued

| 48 | CH | CONH-3-pyridyl | Ph | F |
|---|---|---|---|---|

HERBICIDAL EXAMPLE A (Pre-Emergence)

Seeds of the test species listed below were each sown in 8.5cm square pots filled to within 2cm of the top with sterile loam, and were covered with a 2–5mm layer of loam. The pots were watered, and then treated by application to the soil surface in a spray cabinet with the compounds of the Examples listed below formulated as a solution/suspension in 3:1 by volume of acetone and the wetting agent polyoxyethylene (20 mols) monolaurate solution (10 g per litre). The concentration of each test compound and volume of application were calculated to give the desired rate of application of the compound in 200 litres per hectare.

After 3 to 4 weeks growth in a glasshouse (minimum temperature 16° C. for temperate species, 21° C. for non-temperate species, 16 hours per day photoperiod) the plants were visually assessed for any herbicidal response. All differences from an untreated control were scored accordingly to an index where 0=no effect, 1=–24% effect, 2=25–69% effect, 3=70–89% effect and 4=90–100% effect.

In the table below, the following letters are used to denote the plant species:

a—*Triticum aestivum* (wheat)
b—*Hordeum vulgare* (barley)
c—*Beta vulgaris* (sugar beet)
d—*Brassica napus* (rape)
e—*Alopecurus myosuroides* (blackgrass)
f—*Avena fatua* (wild oat)
g—*Elymus repens* (couch)
h—*Bromus sterilis* (barren brome)
i—*Viola arvensis* (field pansy)
j—*Stellaria media* (chickweed)
k—*Galium aparine* (cleavers)
l—*Matricaria incdora* (scentless mayweed)
m—*Polygonum lapathifolium* (Pale persicaria)
n—*Veronica persica* (Buxbaum's speedwell).

The results obtained were as follows:

| Ex | Kg/ha | a | b | c | d | e | f | g | h | i | j | k | l | m | n |
|---|---|---|---|---|---|---|---|---|---|---|---|---|---|---|---|
| 2 | 0.125 | 4 | 4 | 4 | 4 | 4 | 4 | 4 | 4 | 4 | 4 | 4 | 4 | 4 | 4 |
| 3 | 0.125 | 4 | 3 | 4 | 4 | 4 | 4 | 4 | 4 | 4 | 3 | 4 | 4 | 4 | |
| 10 | 0.125 | 3 | 4 | 4 | 4 | 3 | 4 | 4 | 4 | 4 | 4 | 4 | 4 | 4 | |
| 11 | 0.125 | 4 | 4 | 2 | 4 | 4 | 3 | 4 | 4 | 2 | 4 | 4 | 1 | 4 | 4 |
| 12 | 0.125 | 4 | 3 | 3 | 4 | 4 | 3 | 4 | 4 | 3 | 4 | 3 | 1 | 4 | 4 |
| 13 | 0.125 | 2 | 2 | 3 | 4 | 4 | 1 | 4 | 3 | 3 | 4 | 3 | 3 | 4 | 4 |
| 15 | 0.125 | 3 | 4 | 2 | 3 | 4 | 2 | 4 | 4 | 1 | 3 | 3 | 0 | 4 | 4 |
| 16 | 0.125 | 2 | 2 | 1 | 1 | 2 | 2 | 4 | 2 | 1 | 0 | 3 | 1 | 3 | 3 |

HERBICIDAL EXAMPLE B (Post-Emergence)

The plant species listed below were grown in 8.5cm square pots containing sterile loam in a glasshouse (minimum temperature 16° C. for temperate species, 21° C. for non-temperate species, 16 hours per day photoperiod), and were treated in a spray cabinet at the 2–3 leaf stage with the compounds of the Examples listed below formulated as a solution/suspension in 3:1 by volume of acetone and the wetting agent polyoxyethylene (20 mols) monolaurate solution (10 g per litre). The concentration of each test compound and volume of application were calculated to give the desired rate of application of the compound in 200 litres per hectare.

After 3–4 weeks, the plants were visually assessed for any herbicidal response. All differences from an untreated control were scored according to an index where 0=no effect, 1=1–24% effect, 2=25–69% effect, 3=70–89% effect and 4=90–100% effect.

In the table below, the letters used denote the same plant species as in Herbicidal Example A:

The results obtained were as follows:

| Ex | Kg/ha | a | b | c | d | e | f | g | h | i | j | k | l | m | n |
|----|-------|---|---|---|---|---|---|---|---|---|---|---|---|---|---|
| 2  | 0.125 | 4 | 4 | 4 | 4 | 4 | 4 | 4 | 4 | 4 | 4 | 4 | 2 | 4 | 2 |
| 3  | 0.25  | 4 | 4 | 4 | 4 | 3 | 4 | 4 | 3 | 4 | 4 | 4 | 2 | 4 | 4 |
| 9  | 0.125 | 4 | 4 | 4 | 4 | 4 | 4 | 4 | 4 | 4 | 4 | 4 | 4 | 4 | 4 |
| 10 | 0.125 | 1 | 1 | 2 | 2 | 2 | 0 | 2 | 2 | 3 | 4 | 2 | 0 | 2 | 0 |
| 11 | 0.125 | 4 | 4 | 2 | 3 | 4 | 4 | 4 | 4 | 2 | 4 | 4 | 0 | 4 | 2 |
| 12 | 0.125 | 2 | 4 | 2 | 3 | 4 | 4 | 4 | 3 | 2 | 4 | 4 | 1 | 3 | 2 |
| 13 | 0.25  | 2 | 2 | 2 | 3 | 4 | 3 | 4 | 4 | 1 | 1 | 4 | 0 | 3 | 3 |
| 15 | 0.25  | 4 | 4 | 3 | 4 | 4 | 4 | 3 | 4 | 3 | 4 | 4 | 1 | 4 | 3 |
| 16 | 0.25  | 2 | 2 | 2 | 3 | 4 | 3 | 3 | 3 | 2 | 1 | 3 | 0 | 3 | 2 |
| 19 | 0.125 | 2 | 2 | 2 | 2 | 2 | 2 | 2 | 3 | 1 | 2 | 3 | 0 | 3 | 4 |

We claim:

1. The haloacetic acid derivatives of the formula:

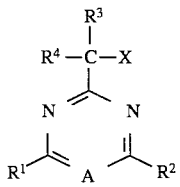

(I)

and salts thereof, where:

A is —N= or —CH=;

X is halo;

$R^1$ and $R^2$, which may be the same or different, each represent alkyl, alkoxy, haloalkyl, haloalkoxy, halo, alkylamino or dialkylamino;

$R^3$ is —CN, —COOR$^5$, —CONR$^6$R$^7$, —CSNH$_2$, —CHO, —CH=Z, —CH(OAlkyl)$_2$, —CH$_2$OH, —CH$_2$OR$^9$, or a substituted or unsubstituted 5- or 6-membered heterocyclic group linked via a ring carbon atom which is between two ring heteroatoms;

$R^4$ is H, or a substituted or unsubstituted alkyl, alkenyl, alkynyl, cycloalkyl, aryl or aralkyl group;

$R^5$ is H, —N=CR$^{6a}$R$^{6b}$, or a substituted or unsubstituted alkyl, alkenyl, alkynyl, cycloalkyl or aralkyl group;

$R^6$ is H, or a substituted or unsubstituted alkyl, alkenyl, alkynyl, cycloalkyl, aryl, aralkyl or heteroaryl group;

$R^7$ is a group as defined for $R^6$ or is —SO$_2$R$^8$, —OH, —CN, —OR$^{10}$, —NH$_2$, or —NHR$^{10}$; or $R^6$ and $R^7$ together form a ring;

$R^8$ is —NR$^{6a}$R$^{6b}$ or a substituted or unsubstituted alkyl, alkenyl, alkynyl, cycloalkyl, aralkyl, aryl or heteroaryl group;

$R^9$ is a substituted or unsubstituted alkyl, alkenyl, alkynyl, cycloalkyl, aralkyl or acyl group;

$R^{10}$ is a group as defined for $R^9$ or is a substituted or unsubstituted aryl or heteroaryl group;

Z is =N—NR$^6$R$^{12}$ or =NOR$^6$;

$R^{12}$ is a group as defined for $R^6$, or is a substituted or unsubstituted acyl group; and $R^{6a}$ and $R^{6b}$, which may be the same or different, are each a group as defined for $R^6$;

with the proviso that, when $R^4$ is ortho-substituted phenyl or naphthyl, any ortho-substituent thereon is halogen, —NO$_2$, —OH, —OR$^{10}$, —SH, —SR$^8$, —SOR$^8$, —SO$_2$R$^8$, —NH$_2$, —NR$^6$R$^{10}$, aryl or heteroaryl.

2. The compounds according to claim 1 in which $R^2$ is methyl, methoxy or difluoromethoxy.

3. The compounds according to any of claim 1 in which X is chlorine, bromine or fluorine.

4. The compounds according to any of claim 1 in which $R^3$ is a group —COOR$^5$ where $R^5$ is alkyl of 1 to 4 carbon atoms.

5. The compounds according to any of claim 1 in which $R^4$ is hydrogen, alkyl of 1 to 4 carbon atoms, or phenyl 6. The compounds according to claim 1, in which $R^1$ and $R^2$, which may be the same or different, each represent alkoxy.

7. The compounds according to claim 1 in which $R^1$ is chloro, methyl, methoxy, difluoromethoxy or ethoxy.

8. The compounds according to claim 7 in which $R^2$ is methyl, methoxy or difluoromethoxy; X is chlorine, bromine or fluorine; $R^4$ is hydrogen, alkyl of 1 to 4 carbon atoms, or phenyl; and in which $R^3$ is a group —COOR$^5$ where $R^5$ is alkyl of 1 to 4 carbon atoms.

9. The compounds according to claim 8 in which $R^1$ and $R^2$ are methoxy and X is fluorine.

10. The compounds according to claim 9 in which A is —CH=, $R^4$ is isopropyl or sec-butyl and $R^5$ is methyl or ethyl.

11. The compounds according to claim 9 in which A is N, $R^4$ is propyl, isopropyl, sec-butyl, CH(C$_2$H$_5$)N$_2$ or CH(CH$_3$)C$_6$H$_5$ and $R^5$ is ethyl.

12. Methyl 2-(4,6-dimethoxypyrimidin-2-yl)-2-fluoro-2-phenylacetate.

13. A herbicidal composition which comprises from 0.01 to 99% by weight of one or more compounds according to any of claim 1, in association with a suitable carrier and/or surface active agent.

14. A herbicidal composition which comprises from 0.01 to 99% by weight of one or more compounds according to claim 8, in association with a suitable carrier and/or surface active agent.

15. A herbicidal composition which comprises from 0.01 to 99% by weight of one or more compounds according to claim 9, in association with a suitable carrier and/or surface active agent.

16. A herbicidal composition which comprises from 0.01 to 99% by weight of one or more compounds according to claim 10, in association with a suitable carrier and/or surface active agent.

17. A herbicidal composition which comprises from 0.01 to 99% by weight of one or more compounds according to claim 11, in association with a suitable carrier and/or surface active agent.

18. A herbicidal composition which comprises from 0.01 to 99% by weight of one or more compounds according to claim 12, in association with a suitable carrier and/or surface active agent.

19. A method of combating weeds at a locus infested or liable to be infested therewith which comprises applying to said locus an effective amount of one or more compounds according to claim 1.

20. A method according to claim 19 in which the amount applied is from 0.001 to 2 kg/ha.

21. A method of combating weeds at a locus infested or liable to be infested therewith which comprises applying to said locus; an effective amount of one or more compounds according to claim 8.

22. A method of combating weeds at a locus infested or liable to be infested therewith which comprises applying to said locus an effective amount of one or more compounds according to claim 9.

23. A method of combating weeds at a locus infested or liable to be infested therewith which comprises applying to said locus an effective amount of one or more compounds according to claim 10.

24. A method of combating weeds at a locus infested or liable to be infested therewith which comprises applying to said locus an effective amount of one or more compounds according to claim 11.

25. A method of combating weeds at a locus infested or liable to be infested therewith which comprises applying to said locus an effective amount of one or more compounds according to claim 12.

* * * * *